United States Patent [19]

Cappellini et al.

[11] Patent Number: 4,939,505
[45] Date of Patent: Jul. 3, 1990

[54] MONITORING AND WARNING SYSTEM FOR SERIES FED-RUNWAY VISUAL AIDS

[75] Inventors: Luigi Cappellini; Cesarino Moretti; Daniele Cappelini, all of Rome, Italy

[73] Assignee: Vitroselenia S.P.A., Rome, Italy

[21] Appl. No.: 220,550

[22] Filed: Jul. 18, 1988

[30] Foreign Application Priority Data

Jul. 29, 1987 [IT] Italy .............................. 48251 A/87

[51] Int. Cl.$^5$ ................... G08B 24/00; G08B 25/00
[52] U.S. Cl. ........................... 340/642; 340/524; 340/525; 340/635; 340/825.11
[58] Field of Search ............ 340/642, 635, 825.11, 340/524, 525

[56] References Cited

U.S. PATENT DOCUMENTS

| | | | |
|---|---|---|---|
| 4,675,574 | 6/1987 | Delflache | 340/642 |
| 4,727,449 | 2/1988 | Fleck | 340/642 |
| 4,808,982 | 2/1989 | Knapp | 340/642 |

*Primary Examiner*—Glen R. Swann, III
*Attorney, Agent, or Firm*—Herbert Dubno

[57] ABSTRACT

A system for failure detection of series-fed lighting circuits monitors the status of series-fed lamps and provides for feedthrough shift circuit protection of the isolating transformer and for suppression of overvoltage which appears at the failed lamp terminals. Current monitoring systems are rendered obsolete by this RLW (Runway Lighting Warning). The RLW system, which consists basically of a control unit equipped with detector probes, utilizes the series-fed lamp supply line, without any need for supplementary lines, and displays the failed lamp identification number accurately. The system has its preferred application in series-fed support lighting systems, but may also find application within any series-fed lighting system such as that of harbors, road networks and so on. A control unit remote from the detectors counts pulses derived from the periodic supply voltage to identify the detector transmitting the warning signal and the detector is provided with scalers and a programmer for transmitting the warning signal when its count matches the assigned count at the control unit.

9 Claims, 9 Drawing Sheets

MONITORING AND WARNING SYSTEM FOR SERIES-FED RUNWAY VISUAL AIDS

FIELD OF THE INVENTION

The present invention relates to a system which monitors the lighting of an airport, or of any other site which requires lighting, such as harbors, road networks, sporting grounds, etc.

The preferred application of the invention is to the airport field because of the requirements for maximum safety which are applied to this field area.

It in fact provides a centralized lamp serviceability check for runways and access paths.

This monitoring system is essentially an electronic facility which, without any additional cabling or modification of the supply network for the lamps makes use of the series-connected lamp supply line and can display with accuracy the identification number of the failed lamp and provide for by-pass of the failed lamp and of the relevant isolating transformer and also for suppressing excess voltages.

OBJECT OF THE INVENTION

The object of this invention is to provide for checking remotely all lamps fitted to the circuit and displaying the failed lamp location number accurately, without requiring recourse to scheduled inspection routines.

In the event of one or more lamps' failing, the system has a self-resetting device which short circuits the relevant isolating transformer and suppresses excess voltages, so as to eleminate the need for the replacement of fused film cutouts, which would otherwise burn out upon intervention.

The system therefore is essentially made up of a control unit and of one or more bypass and suppressor detectors, used separately or jointly in the same housing and, by comparison with previous systems, provides safety and cost advantages.

The uniqueness of this invention is in the fact that the detector probes have built-in short circuit bypass and snubbers.

As a result, also effective protection to maintenance personnel is provided, even when the circuit is live.

BACKGROUND OF THE INVENTION

Previous solutions, may be summarized as follows:

(1) systems which provide only indication of the percentage of failed lamps and therefore require inspection to locate individual failed lamps, and inspection routines At high cost; and (2) systems which check each single lamp by means of detectors, connected with a data collection center by means of additional lines which results in higher costs and may, at times, be impossible to implement.

SUMMARY OF THE INVENTION

The multiplicity of series-fed lamps is monitored and controlled by:

(a) feeding the supply circuit with a periodic voltage from a constant-current generator over mains conductors;

(b) inductively detecting at a central control unit remote from the lighting circuits and from at least one of the mains conductors a first signal representing periodicity of the source and time-spaced second signals representing status of the lighting circuits;

(c) generating at the control unit counting pulses from the first signal and determining from a count of the pulses which of the lighting circuits is represented by a specific one of the second signals;

(d) at each of the lighting circuits in a respective detector probe, generating a first signal representing periodicity of the source and forming a respective count from the first signal at each detector probe representing the respective lighting circuit;

(e) upon failure of a lamp at a respective one of the lighting circuits, generating a warning signal and transmitting the warning signal over at least one of the mains conductors upon the formation of the respective count at the one of the lighting circuits matching a count at the control unit representing the one of the lighting circuits;

(f) inductively detecting at the control unit the warning signal transmitted by the one of the lighting circuits and, upon the count at the control unit matching the count at the detector probe of the one of the lighting circuits, displaying at the control unit an identification of the one of the lighting circuits with a warning indication of failure of the respective lamp; and (g) upon failure of the lamp at the one of the lighting circuits, suppressing any voltage surge resulting from the failure and applying a short circuit across the failed lamp.

The system itself can comprise:

a constant-current source connected to the series-connected lighting circuits by mains conductors and supplying a periodic voltage thereto;

a control unit remote from the lighting circuits and comprising:

an inductive pickup coupled to at least one of the conductors and deriving therefrom a first signal representing periodicity of the voltage and a second signal representing a warning of failure of a particular one of the lighting circuits, pulse-generating means operatively connected to the pickup for producing countable pulses from the first signal, means including a plurality of scalers and a programmable selector for registering counts assigned to the lighting circuit whereby each of the lighting circuits is assigned a respective count, a tuned circuit operatively connected to the pickup for detecting a warning signal from the one of the lighting circuits, and means operatively connected to the tuned circuit and to the means including the plurality of scalers and the programmable selector and provided with a display for displaying an identification of the one of the lighting circuits and a warning of failure thereof upon receipt by the control unit of a warning signal transmitted by the one of the lighting circuits; and a respective detector probe connected to each of the lighting circuits, the detector probes each comprising:

a coupling circuit connecting the detector probe to the respective lighting circuit, a pulse detector operatively connected to the coupling circuit for generating countable pulses representing periodicity of the periodic voltage, means including a plurality of scalers and a programmable selector operatively connected to the pulse detector for registering counts assigned to the respective lighting circuit, means operatively connected to the coupling circuit and responsive to lamp failure at the respective lighting circuit and including an oscillator for outputting a warning signal upon lamp failure, transmitter means operatively connected to the means for outputting the warning signal and to the means for registering counts assigned to the respective lighting circuit for applying the warning signal to the conductors upon a count registered at the detector probe of the one of the lighting circuits matching a count at the control unit assigned to the respective one of the lighting circuits, means connected to the respective lighting circuit for suppressing voltage surges, and means operatively connected to the respective lighting circuit for forming a bypass short circuit across a failed lamp at the respective lighting circuit.

According to a feature of the invention, the detector probe, surge voltage suppressor and the bypass short circuit device and the connector connecting it to the lighting circuit are housed in a common container which may be made of polycarbonate or like insulating material and can be hermetically sealed and ribbed to provide for cooling. The connector may be formed integrally with the housing in the same mold.

The inductive pickup may surround one of the mains conductors so that it is coupled to the high voltage supply line without direct contact.

The control circuit can be provided with inhibiting means for suppressing one or more supply cycles from the constant current source.

The failure detector warning may be the absence of a signal and an indication of any failure may be provided. Such failures include failuree of the lamp, of the isolating transformer, of the cables, of the lamp holder, of the detector probe or the like.

BRIEF DESCRIPTION OF THE DRAWING

The above and other objects, features and advantages of my invention will become more readily apparent from the following description, reference being made to the accompanying highly diagrammatic drawing in which.

DESCRIPTION

Figure 1:
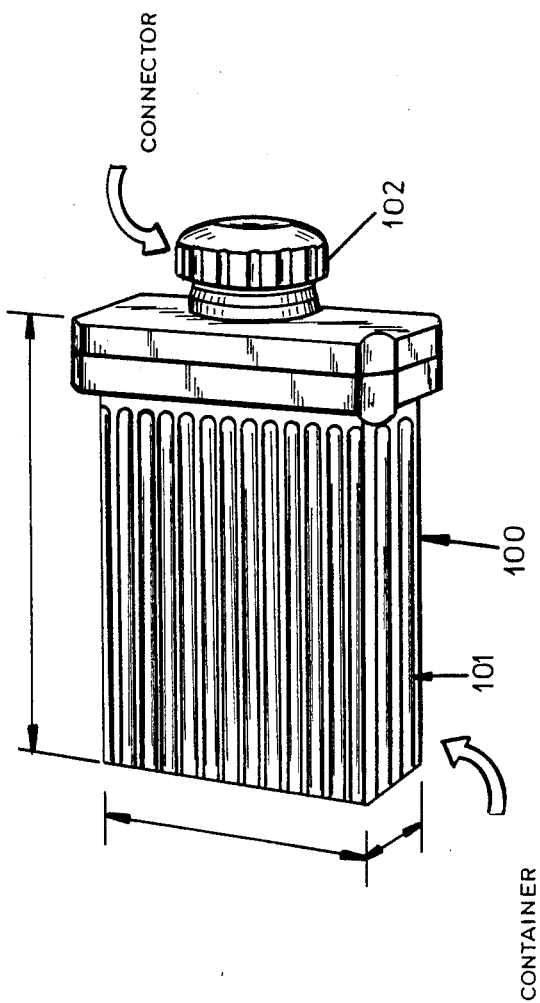
FIG. 1 is a perspective view of a detector unit according to the invention.

FIG. 1 shows the architecture of a detector probe according to the invention which comprises a housing 100 formed with heat disipating ribs 101 and molded integratable with a connector 102. The housing may be provided with all of the circuit elements illustrated in FIG. 9.

Figure 2:
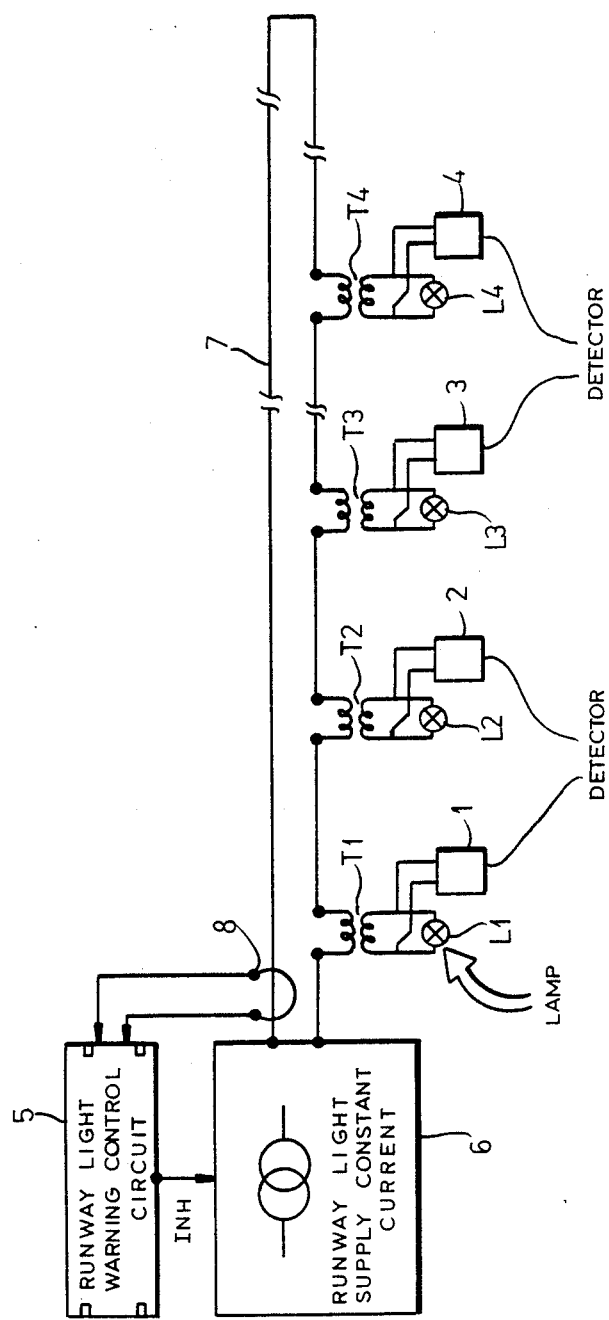
FIG. 2 is a block diagram, partly in schematic form, illustrating runway lighting provided with the failure detector system of the invention.

The principles of the invention will be apparent from FIG. 2 which shows a constant current power supply source and regulator 6 feeding a series circuit 7 formed by the primaries of individual isolating transformers T1, T2, T3, T4, the secondaries of which energized lamps L1, L2, L3, L4, respectively. The detector probes 1 2, 3, 4, are respectively connected across these lighting circuits. The detector probes are shown in detail in FIG. 9. It suffices at this point to observe that the control unit 5 is connected to the series circuit 7 inductively by the pickup 8 (see FIG. 5) and generates a count from the periodic voltage of the source 6 which, through the use of a programming circuit, is associated with the respective lighting circuits T1, L1; T2, L2; T3, L3 and T4, L4 in the detectors 1-4 of which corresponding counts have been programmed. When the counts of a detector probe 1-4 matches this count at the control unit 5, a display is operated.

Figure 8:
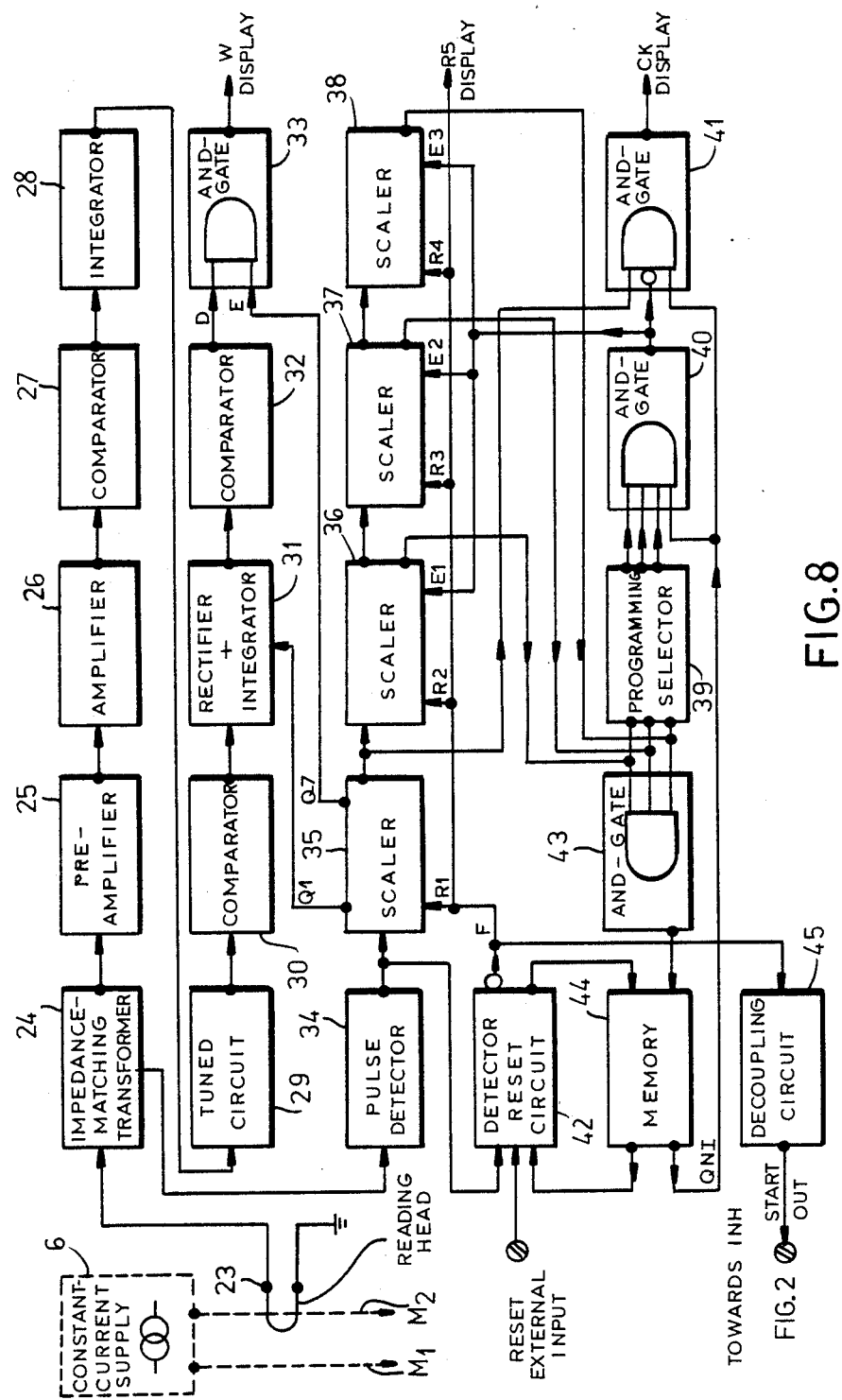
FIG. 8 is a block diagram of the control unit.
Figure 9:
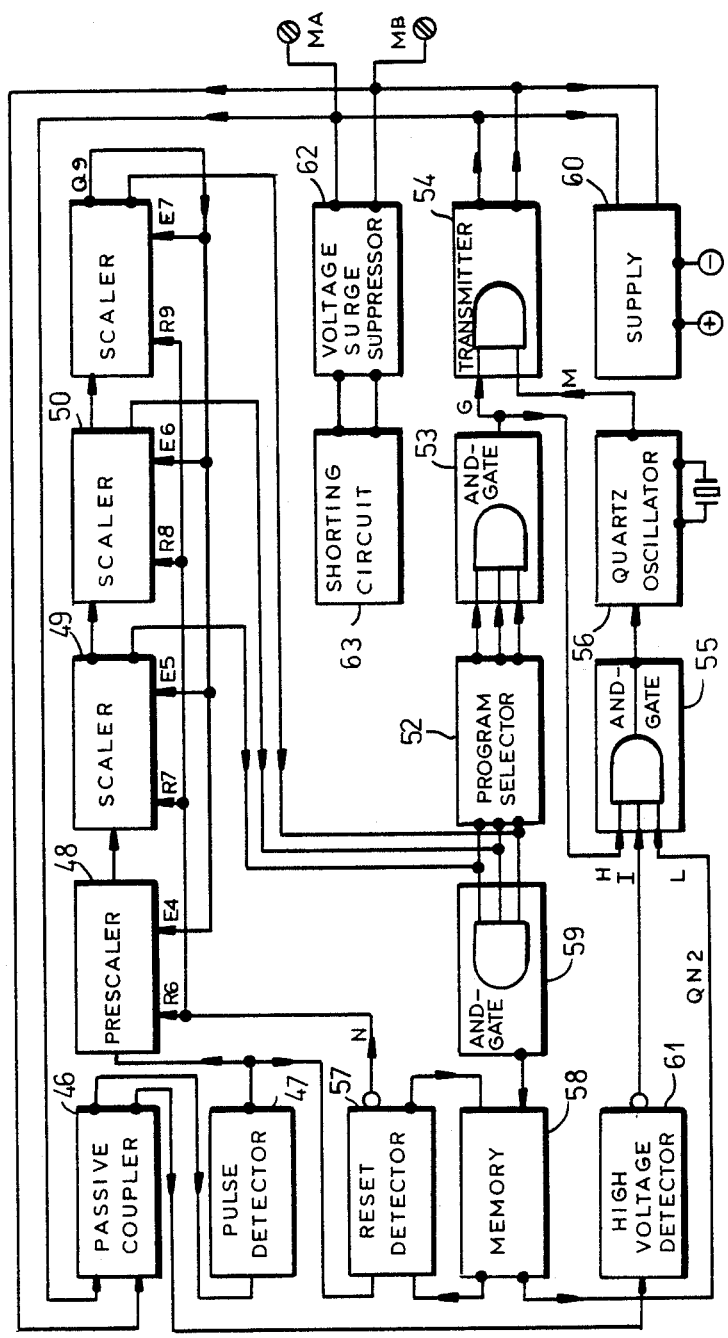
FIG. 9 is a block diagram of the detector probe.

While for the circuits of FIGS. 8 and 9, the warning signal which is transmitted is generated by an oscillator (FIG. 9) and is picked up by a tuned circuit (FIG. 8), it will be understood that the absence of any specific signal may also be used as a warning of lamp failure.

An inhibiton signal INH applied to the power supply 6 may cut out the supply for a number of cycles to restart the operation for monitoring the runway lights.

Figure 3:
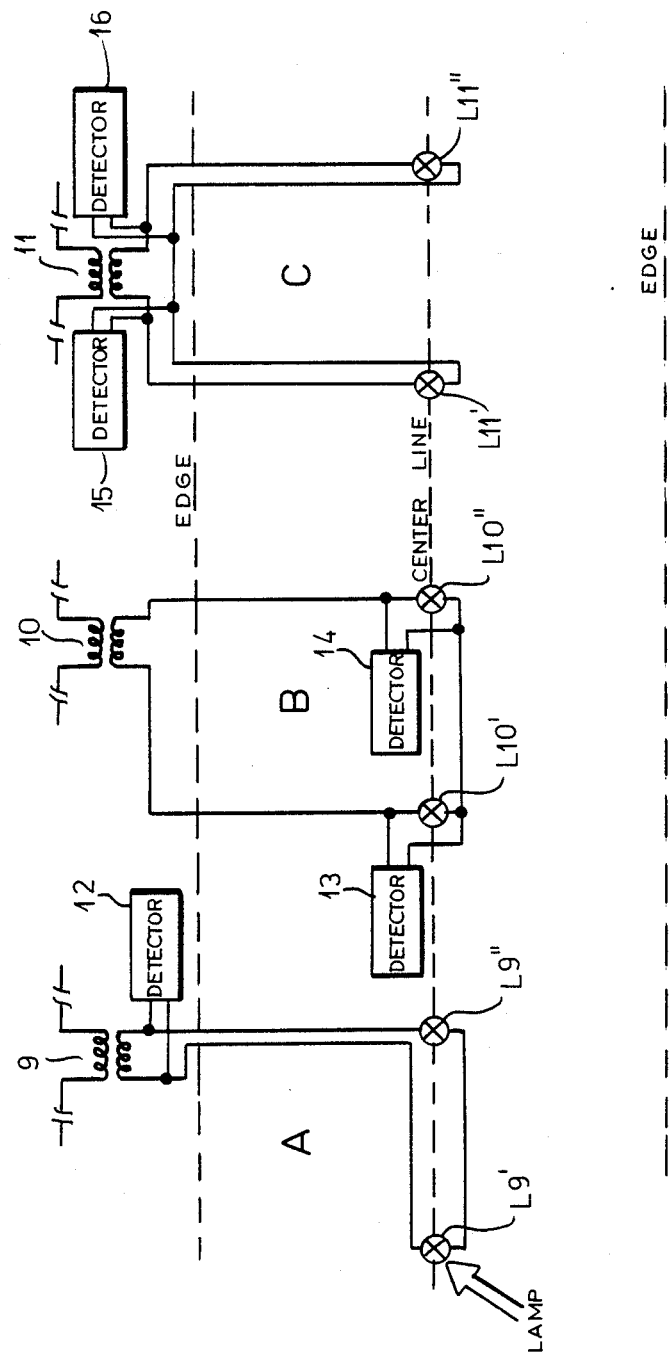
FIG. 3 is a diagram similar to FIG. 2 but showing a number of different arrangements of the lighting circuits which can be monitored in accordance with the invention.

FIG. 3 shows that a single isolating transformer 9 may feed two lamps L9' and L9" connected in series and that one detector probe 12 can be connected across the series circuit of these lamps. In this case, upon failure of any one of the two lamps, the secondary of the transformer will be shorted even though the remaining lamp is effective, and a failure signal will be transmitted.

So that the operationable lamp will not be extinguished, which would further degrade runway security, the isolating transformer 10 is shown to have its secondary connected in series with the lamps L10' and L10", but respective detectors 13 and 14 are connected across these lamps and short only the defective lamp while transmitting respective failure signals depending upon which of the two lamps is shorted. The detectors 13 and 14 are located in the vicinity of the lamps at the center of the runway.

For network C, the detectors 15 and 16 are located in the proximity of the transformer 11 at the edge of the runway and hence are somewhat more remote from the lamps L11' and L11".

Figure 4:
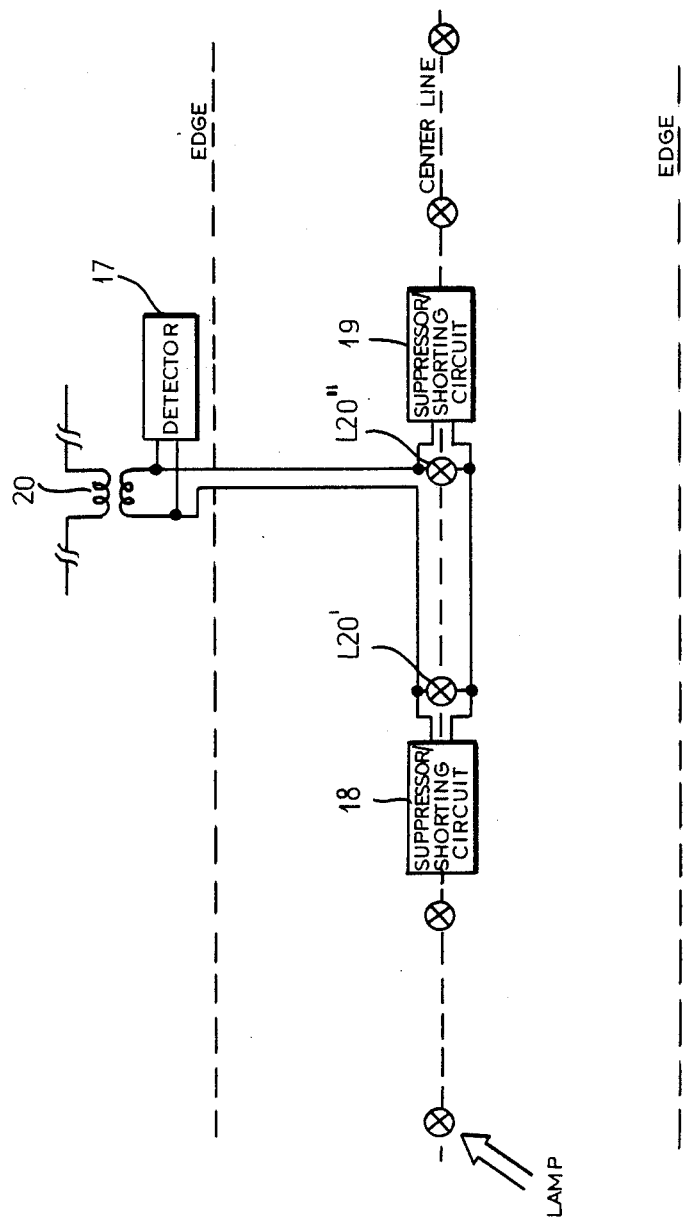
FIG. 4 is a view similar to FIG. 3 illustrating a different arrangement of the high voltage suppressor and the bypass short circuiting system.

In the embodiment of FIG. 4, the isolating transformer 20 feeds the lamps L20' and L20" and a single detector 17 is provided along the edge of the runway proximal to the transformer 20. However, each of the lamps L20' and L20" is provided with a surge suppressor and shorting circuit respectively represented at 18 or 19. In this case, of course, the surge suppressor and shorting circuit need not be included in the housing of the detector probe 17 (compare FIG. 1).

Figure 5:
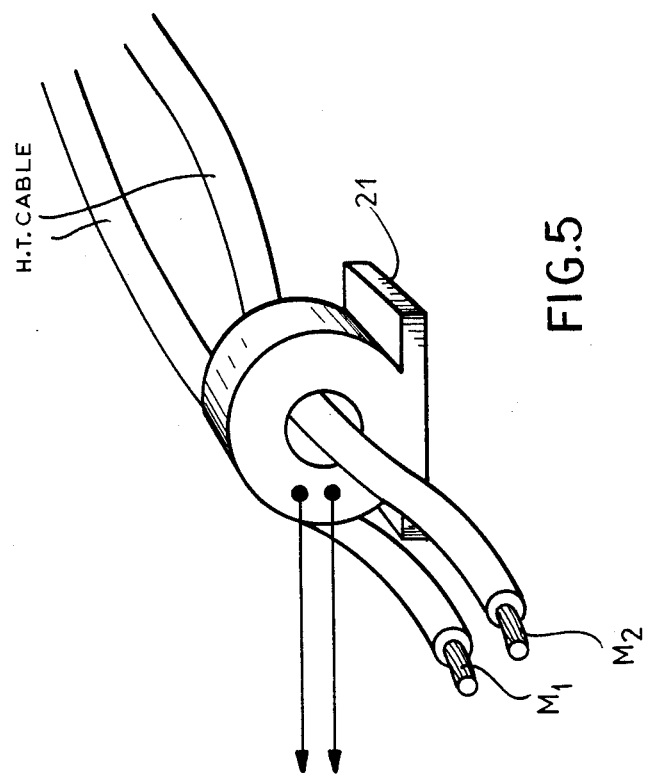
FIG. 5 is a perspective view of the inductive pickup used in the system of FIG. 2 and the circuit of FIG. 8.
Figure 6:
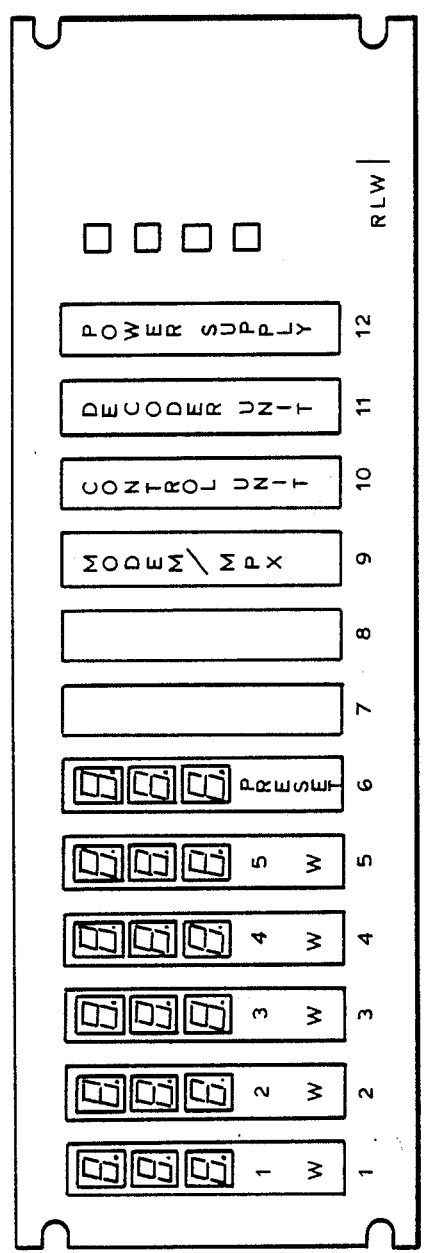
FIGS. 6 and 7 show the panels of two control units of the invention, including the display, for monitoring of a single constant current regulator and a number of constant current regulators, respectively.
Figure 7:
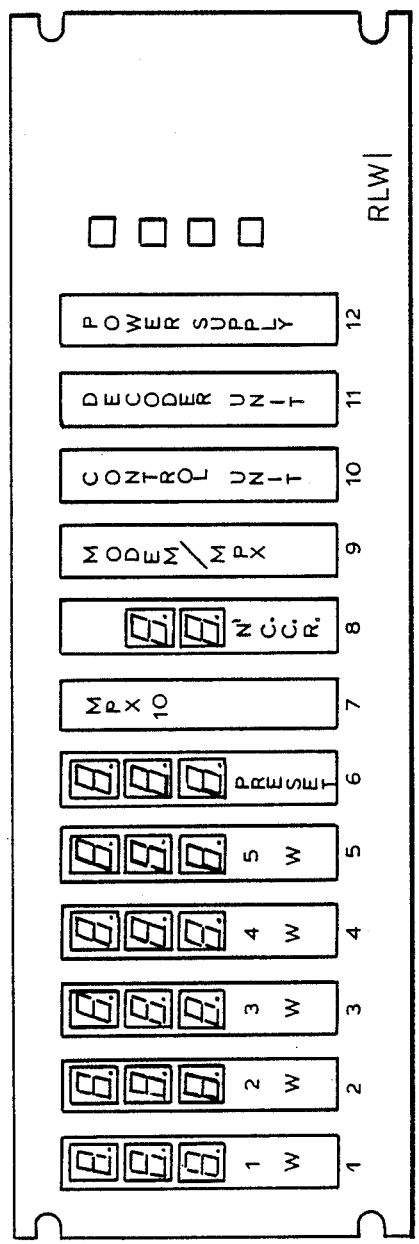

The inductive pickup 21 of FIG. 5 is shown to surround one of the pairs of mains conductors M1 and M2 connecting the power supply 6 to the series circuit 7 (FIG. 2) and the display panels of FIGS. 6 and 7 can, of course, be used with the control unit 5 which is shown in greater detail in FIGS. 8 and 9.

The control unit 5 of FIG. 8 has a pickup 23, which can be the same as the pickup 21 of FIG. 5, connected to one of the mains conductors M1 and M2 from the constant current supply source 6 and input to the impedance matching transformer, an output of which is connected to the preamplifier 25 feeding amplifier 26, comparator 27, integrator 28, tuned circuit 29, comparator 30, integrator 31, comparator 32 and an AND gate 33 outputting to the display, e.g. the panel of FIG. 6 or the panel of FIG. 7.

The impedance matching transformer or coupling circuit 24 also supplies the pulse detector 34 which generates the countable pulses applied to the scalers 35 to 38 which cooperate with the program selector to select the monitor detector probes. For this purpose, a detector reset circuit 42 and a memory 44 with AND gates 40, 41 and 43 are provided. The display is activated through the AND gate 41 and decoupling circuit 45 is likewise provided.

In many respects, the circuit of FIG. 9 is similar to that of FIG. 8 since it uses scalers 48 to 41 connected to the respective lighting circuit through the pulse detector 47 and the coupler 46, in cooperation with the memory 58, the reset detector 57 and AND gate 59, the program selector 52 and an AND gate 53 to register a count representing the particular detector probe and hence the particular lighting circuit.

The passive coupler also provides the input to a high voltage detector which is protected by an AND gate 55 and a quartz oscillator 56 to the transmitter 54 for generating the warning signal upon lamp failure. A voltage supply for this circuit is represented at 60 and the bypass shorting circuit and the voltage surge suppressor at 63 and 62 respectively.

In the following, as a non limiting example, the description of the invention with reference to FIGS. 8 and 9, is given. Constant current regulator 6 (FIG. 8), which forms part of the monitored network, is shown in dashed lines.

The system uses a reading head 23 which, inductively coupled to one of the high voltage cables, reads the lamps supply waveform and the envelope of the reply signal which all detectors in the system feed back to the cable, according to a pre-established sequence, only when the lamp is operational. If the lamp is burned out or off for other reasons, the detector will not operate and because the current-induced signal is missing, the control unit will provide a warning as described below.

Information from pick-up 23 is coupled by an impedance matching transformer 24 which has suitable suppressor devices which reduce amplitudes to prevent destruction of the other electronic circuits of the system, to a first preamplifier 25. The first amplifier 25 preamplifies linearly the weak signal which each detector in turn inserts on line and supplies it with the correct amplitude at the input of a second amplifier 26, which is a non linear, low signal amplifier and passes an output to a comparator 27 only if its level is above a typical noise threshold present on the high voltage line.

Comparator 27 outputs the high frequency signals of the detectors together with the low frequency transients caused by closing and opening of the SCR semiconductors or of other components used in the constant current generator of the lamp.

Therefore all signals, useful or not, are present at the output of comparator 27 only if their levels match the comparison voltage.

The purpose of comparator 27 is to ensure that the control unit is insensitive to low signals.

Comparator 27 provides squared signals, with constant amplitude, only if they pass a well defined value at the input.

All waveforms provided by comparator 27, either rectangular or square, are sent to circuit 28 which is an active integrator with suitable amplitude limiting feedback, which transforms the input to a triangular output signal with constant amplitude.

In particular, circuit 28 converts to triangular waves all square waves so that their lowest harmonic content causes tuned circuit 29 to resonate at lower, even or odd harmonics.

Therefore, at the output of tuned circuit 29 there appears only a resonating frequency having the highest sine amplitude value and it alone will be compared with and will exceed the comparison voltage of comparator 30.

Comparator 30 provides a square wave at the resonating frequency which is the same as that used as detector reply and is sent to rectifier bridge 31 with a charge capacitor used as integrator, with a staircase charging pattern.

As each detector message includes a high frequency signal enveloped over a few mains cycles, the integrator charge time in circuit 31 is tailored so that only when 50% of mains cycles are passed, can the integrator reach the level required to meed the level of the last comparator of chain 32, which will provide AND gate 33 with an enable signal for the entire duration of the detector signal, which is sent to input D.

Coupling circuit 24 also sends mains data to a pulse detector 34 which generates a pulse for each mains cycle to drive a first scaler 35, the output of which, suitably divided, provides the clock pulse to drive all following scalers 36, 37, 38 and the timing for detectors to provide reply signals. This first scaler 35 will also provide ancillary signals such as: signal Q1 sent to integrator 31 which serves to reset the staircase integrator at the start of a transmission cycle of each detector; and signal Q7 sent to output E of AND circuit 33, which serves to monitor, for short times, 70% of transmission time, whether output of comparator 32 is high or low so that the output from AND circuit 33 provides a warning signal W if D is low.

The control unit has the following scalers; 36 (units); 37 (tens) 38 (hundreds) which count the pulses provided by first counter or scaler 35. Three programming selectors 39, for units, tens and hundreds are programmed purposely to stop counting by an AND circuit 40 when it has reached the number of detectors to be checked. Via AND 41 circuit, also counting pulses CK, display drivers for warning indication which shift with counters 36, 37, 38 are stopped.

Pulses provided by detector 34 are integrated in circuit 42 and normally keep the output F of the reset detector circuit 42 at a level such that counters 35, 36, 37, 38 can operate.

Therefore circuit 42 has an integrator with a constant discharge time which, when an input fails for one or more cycles, is such that circuit actuates resets R1, R2, R3, R4 and R5 of all counting and measurement circuits, including displays. This temporary lack of input may be purposely caused from outside when one wishes to update the monitoring by means of the Reset External input command.

Upon switch-on of the constant current generator, reset detector circuit 42 also provides a soft start pulse to memory 44 so that output QN1 inhibits output CK of AND circuit 41 to the displays.

This soft start device has been purposely fitted to give the field detector probes time enough to reach the required supply voltage and to perform monitoring at least 30 seconds after switch-on, which is considered the most critical for lamp filaments.

Monitoring will be performed when AND circuit 43 is enabled and that is only when their respective inputs are simultaneously high and coincident as a result of the delay set.

A suitable de-coupling circuit 45, provides a start out output to be sent to inhibit input INH (FIG. 2) of the constant current generator.

FIG. 9 shows in block form, the main functional elements of the detector probes and which are needed to inspect, on-line, the signal which informs the control unit whether the lamp is serviceable. This FIG. also shows the by-pass and suppressor circuits.

The detector probe is wired in parallel with the lamp by means of terminals MA, MB (shown on the right side of the block diagram).

The reset circuit and its related counting circuits are almost identical and therefore synchronous with those housed within the control unit so that the detector probe, when reaching its enabling turn at the time set by the counter, can inject its signal on-line, so that the control unit will classify such time with an identification number by virtue of the fact that it adopts the same count and moves in step with it.

The signal which powers the lamps, is detected by passive coupler 46, whose output drives pulse detector 47, which can extract, under all power conditions, a pulse for each mains cycle and use the detected pulse to drive a first prescalar 48, the output of which, suitably divided, will provide the clock pulse for all following scalers 49,50,51 and the timing for the detector probe to send the lamp status signal.

The probe is therefore provided with scaler 49 for units, scaler 50 for ten, and scaler 51 for hundreds, which serve to count the pulses provided by prescaler 48. Three-program selector 52 for units, tens, hundreds is suitably set to form the correct identification number.

When the programmed number is reached, the three inputs of AND circuit 53 become high simultaneously, and only then is AND circuit 53 effective to activate input G of transmitter 54 and input H of AND 55, which when its other inputs I and L allow, will activate quartz oscillator 56, which modulates input M of transmitter 54 for the entire period set by prescaler 48.

Scalers 48, 49, 50, 51 stop counting upon reaching full scale indication Q9 of counter 51 and by means of its enable inputs E4, E5, E6, E7 connected in parallel. This is for probes which do not have to operate cyclically.

Counting and transmission may be re-started at any time by effect resets R6, R7, R8, R9 caused at each switch on of the constant current generator or when stimulated by the lack of one or more sinusoidal supply cycles.

The mains pulses selected and present at the output of pulse detector 47 are integrated in circuit 57 and keep output N of reset detector 57 low so that scalers 48, 49, 50, 51 may operate.

The discharge constant of the integrator contained in 57 is equal to that of the control unit, and is such that in presence of a temporary power failure of more than one or more cycles, reset detector 57 resets counting, as also happens at the control unit.

Upon power up of the constant current generator feeding the lamps, reset detector 57 also provides for a soft start pulse to be sent to memory 58 so that QN2 inhibits input L of AND 55, so that quartz generator 56 is blocked and lamp serviceability signal is not transmitted.

As mentioned in the description of the control unit (FIG. 8) the soft start device has been purposely fitted to give supply 60 enough time to reach the required voltage and to monitor and transmit the signal after the 30 second delay set on the control unit.

Scaler resetting to start monitoring is given when allowed by AND circuit 59, i.e. when its inputs are simultaneously high and coincident as a function of the delay set.

The high voltage pulse detector 61 has the task to detect voltage surges due to a failed lamp and to keep input I of AND 55 inhibited so that the probe cannot transmit. This event is recognized by the control unit as a warning of failed lamp. The detector probe has two accessory circuits 62 and 63 which dissipate the surge voltages present and apply a short circuit between clamps MA and MB.

The first circuit 62 essentially responds to the leading edge of the pulse, while the second parallel active circuit 63, withstands high transient currents and keeps clamps MA and MB shorted, replacing the failed lamp, so that current may circulate for long times or until normal conditions are restored, in which case the circuit is automatically reset.

We claim:

1. A method of monitoring and controlling a multiplicity of series-fed lighting circuits, each having a lamp connected by an isolating transformer to a supply circuit in which primaries of said transformers are connected in series, said method comprising the steps of:
    (a) feeding said supply circuit with a periodic voltage from a constant-current generator over mains conductors;
    (b) inductively detecting at a central control unit remote from said lighting circuits and from at least one of said mains conductors a first signal representing periodicity of said source and time-spaced second signals representing status of said lighting circuits;
    (c) generating at said control unit counting pulses from said first signal and determining from a count of said pulses which of said lighting circuits is represented by a specific one of said second signals;
    (d) at each of said lighting circuits in a respective detector probe, generating a first signal representing periodicity of said source and forming a respective count from said first signal at each detector probe representing the respective lighting circuit;
    (e) upon failure of a lamp at a respective one of said lighting circuits, generating a warning signal and transmitting said warning signal over at least one of said mains conductors upon the formation of said respective count at said onee of said lighting circuits matching a count at said control unit representing said one of said lighting circuits;
    (f) inductively detecting at said control unit the warning signal transmitted by said one of said lighting circuits and, upon the count at said control unit matching the count at the detector probe of said one of said lighting circuits, displaying at said control unit an identification of said one of said lighting circuit with a warning indication of failure of the respective lamp; and (g) upon failure of said lamp at said one of said lighting circuits, suppressing any voltage surge resulting from said failure and applying a short circuit across the failed lamp.

2. A failure-detection system for a multiplicity of series-fed lighting circuits each having at least one lamp, and an isolating transformer energizing said lamp and having a primary connected in a series circuit with primaries of the isolating transformers of the other lighting circuits, said system comprising:

a constant-current source connected to said series circuit by mains conductors and supplying a periodic voltage thereto;

a control unit remote from said lighting circuits and comprising:

an inductive pickup coupled to at least one of said conductors and deriving therefrom a first signal representing periodicity of said voltage and a second signal representing a warning of failure of a particular one of said lighting circuits, pulse-generating means operatively connected to said pickup for producing countable pulses from said first signal, means including a plurality of scalers and a programmable selector for registering counts assigned to said lighting circuits whereby each of said lighting circuits is assigned a respective count;

a tuned circuit operatively connected to said pickup for detecting a warning signal from said one of said lighting circuits, and means operatively connected to said tuned circuit and to said means including said plurality of scalers and said programmable selector and provided with a display for displaying an identification of said one of said lighting circuits and a warning of failure thereof upon receipt by said control unit of a warning signal transmitted by said one of said lighting circuits; and a respective detector probe connected to each of said lighting circuits, said detector probes each comprising:

a coupling circuit connecting the detector probe to the respective lighting circuit, a pulse detector operatively connected to said coupling circuit for generating countable pulses representing periodicity of said periodic voltage, means including a plurality of scalers and a programmable selector operatively connected to said pulse detector for registering counts assigned to the respective lighting circuit, means operatively connected to said coupling circuit and responsive to lamp failure at the respective lighting circuit and including an oscillator for outputting a warning signal upon lamp failure, transmitter means operatively connected to said means for outputting said warning signal and to said means for registering counts assigned to the respective lighting circuit for applying said warning signal to said conductors upon a count registered at said detector probe of said one of said lighting circuits matching a count at said control unit assigned to said respective one of said lighting circuits, means connected to the respective lighting circuit for suppressing voltage surges, and means operatively connected to the respective lighting circuit for forming a bypass short circuit across a failed lamp at the respective lighting circuit.

3. The system defined in claim 1 wherein all of the means of said detector probe are housed in a common container.

4. The system defined in claim 3 wherein said container is composed of polycarbonate insulating material, is hermetically sealed, is ribbed to provide for cooling and has a connector integrally molded in said material.

5. The system defined in claim 2 wherein said control unit has a pickup surrounding only one of said conductors.

6. The system defined in claim 2 wherein said lamp circuits have lamps arrayed along an airport runway.

7. The system defined in claim 2, further comprising means at said control unit inhibiting said constant current source for a plurality of cycles of said periodic voltage to signal failure.

8. The system defined in claim 2 wherein said probes are connected directly to terminals of the respective isolating transformer.

9. The system defined in claim 2 wherein said pulse generating means includes a pulse detector at said control unit, the first-mentioned means including a plurality of scalers and a programmable selector including a memory receiving input from said selector and said scalers through an AND gate and outputting a signal through at least one further AND gate to a display and a reset detector circuit connected to said memory and to said scalers, said tuned circuit being connected to said pickup through an integrator, a comparator and amplifier.

* * * * *